United States Patent
Lenzenhuber (10) Patent No.: US 11,284,962 B2
(45) Date of Patent: Mar. 29, 2022

(54) RESORBABLE PACKAGING FOR A MEDICAL PRODUCT

(71) Applicant: Aesculap AG, Tuttlingen (DE)

(72) Inventor: Frederick Lenzenhuber, Tuttlingen (DE)

(73) Assignee: AESCULAP AG, Tuttlingen (DE)

(*) Notice: Subject to any disclaimer, the term of this patent is extended or adjusted under 35 U.S.C. 154(b) by 0 days.

(21) Appl. No.: 17/283,399

(22) PCT Filed: Oct. 15, 2019

(86) PCT No.: PCT/EP2019/078013
§ 371 (c)(1),
(2) Date: Apr. 7, 2021

(87) PCT Pub. No.: WO2020/079028
PCT Pub. Date: Apr. 23, 2020

(65) Prior Publication Data
US 2021/0338358 A1    Nov. 4, 2021

(30) Foreign Application Priority Data
Oct. 16, 2018  (DE) .................... 10 2018 125 610.8

(51) Int. Cl.
*A61B 50/33* (2016.01)
*A61B 50/20* (2016.01)
*B65D 75/36* (2006.01)
*A61B 50/30* (2016.01)

(52) U.S. Cl.
CPC .............. *A61B 50/33* (2016.02); *A61B 50/20* (2016.02); *B65D 75/366* (2013.01); *A61B 2050/3004* (2016.02)

(58) Field of Classification Search
CPC . A61B 50/33; A61B 50/20; A61B 2050/3004; B65D 75/366
USPC ..................... 206/363, 524.1, 524.3, 524.4
See application file for complete search history.

(56) References Cited

U.S. PATENT DOCUMENTS

| 5,868,244 A * | 2/1999 | Ivanov .................... B65B 11/50 |
| | | 206/63.3 |
| 9,023,114 B2 * | 5/2015 | Buevich .................. A61N 1/375 |
| | | 623/23.75 |
| 11,000,356 B2 * | 5/2021 | Folger ................ A61B 17/7004 |
| 2009/0193764 A1 | 8/2009 | Elliott et al. |

(Continued)

FOREIGN PATENT DOCUMENTS

| DE | 102013004168 A1 | 9/2014 |
| DE | 202016105248 U1 | 12/2016 |

(Continued)

OTHER PUBLICATIONS

Written Opinion received in Application No. PCT/EP2019/078013, dated Nov. 28, 2019, with translation, 8 pages.

(Continued)

*Primary Examiner* — Jacob K Ackun
(74) *Attorney, Agent, or Firm* — Culhane Meadows PLLC; Christopher A. Rothe (57) ABSTRACT

A packaging, in particular sterile packaging, for a medical product, includes a receiving space for the medical product. A portion of the packaging facing the receiving space is made at least in part, preferably entirely, of a resorbable material.

11 Claims, 5 Drawing Sheets

(56) References Cited

U.S. PATENT DOCUMENTS

| | | | | |
|---|---|---|---|---|
| 2009/0266728 A1* | 10/2009 | Turner | .................. | A61B 90/92 |
| | | | | 206/363 |
| 2013/0327663 A1* | 12/2013 | Telford | ................. | A61B 46/23 |
| | | | | 206/363 |
| 2014/0251845 A1 | 9/2014 | Roesler | | |
| 2014/0319000 A1* | 10/2014 | Fishberger | ............. | A61B 46/10 |
| | | | | 206/389 |
| 2016/0251117 A1* | 9/2016 | Gilpatrick | .............. | B65D 77/20 |
| | | | | 206/524.3 |
| 2020/0197149 A1* | 6/2020 | Folger | ................ | A61B 17/7004 |
| 2021/0196443 A1* | 7/2021 | Folger | ................ | A61B 17/7004 |

FOREIGN PATENT DOCUMENTS

| | | |
|---|---|---|
| EP | 2292528 A1 | 3/2011 |
| JP | 2008500097 A | 1/2008 |
| WO | 2005118066 A2 | 12/2005 |
| WO | 2015166240 A2 | 11/2015 |

OTHER PUBLICATIONS

International Search Report received in application No. PCT/EP2019/078013, dated Nov. 28, 2019, with translation, 5 pages.
Search Report received in German application No. 10 2018 125 610.8 dated Jul. 9, 2019, with translation, 18 pages.
Office Action received in Japanese Application No. 2021-520554 dated Nov. 1, 2021, with translation, 8 pages.

* cited by examiner

RESORBABLE PACKAGING FOR A MEDICAL PRODUCT

CROSS-REFERENCE TO RELATED APPLICATIONS

This application is the United States national phase entry of International Application No. PCT/EP2019/078013, filed Oct. 15, 2019, and claims the benefit of priority of German Application No. 10 2018 125 610.8, filed Oct. 16, 2018. The contents of International Application No. PCT/EP2019/078013 and German Application No. 10 2018 125 610.8 are incorporated by reference herein in their entireties.

FIELD

The present invention relates to a package, in particular a sterile package, for a medical product, comprising a receiving space for the medical product. It also relates to a packaging unit containing such a product.

BACKGROUND

For packaging medical products, various packages and devices are known. Packages of medical products such as implants and tools with pointed and/or sharp operative portions, for example in the form of cutting or sawing edges, milling heads and drills or thread portions, are subject to special requirements. In addition to protecting the packaged product from undesirable influences such as contamination and damage, it is also necessary to protect users from injury before and in particular after use of the product.

With regard to the protection of the product, it should be noted that in the case of medical products packaged in an outer packaging, there is a general risk of accidental contact between the product and parts of the package. In particular, when sharp operative portions come into contact with the packaging material, abrasion can occur so that parts and/or particles of the packaging material adhere to the product and can be transferred to a patient via the product. The preceding problem is particularly relevant for products such as implants or surgical tools. Such products generally have sharp body contours or cutting edges which, in case of contact, in particular already during handling (removal of the product from the package) with the outer packaging, can remove material from the latter, for example in the form of minute particles. Such material components then generally adhere to the product in a hardly perceptible manner or in a manner not perceptible at all and can be introduced into the body of a patient in a detrimental manner in the context of an intended use of the product, such as in the context of use during an operation. It is possible that these material particles remain in the patient and can, in the worst case, cause inflammatory reactions, allergic reactions and the like.

Packages are known from the prior art in which the medical device is held firmly and/or in a defined position, but which cannot satisfactorily solve the problem described above. An example of such packaging is a blister package with a clamp in the coupling area of a product in the form of a tool in order to position and hold the product in a defined position in the package. One disadvantage is that, if external influence on the blister pack combined with its relatively low stability causes the clamping of the tool therein to become loose, the tool can slip in the package and, in particular, hit the package with its sharp operative edges. As already explained in DE 10 2013 004 168 A1, this can cause microfine particles of the package to enter the area of the cutting edges of the tool in an undesirable manner and can possibly cause them to be introduced from there into a surgical wound, which can lead to severe tissue irritation. As a result, such packages can only solve the problem described above to a limited extent, since contamination by packaging material can occur in particular during handling of the product while it is being removed from the outer packaging.

In order to improve these circumstances, DE 10 2013 004 168 A1, provides a package of sterile surgical tools in which the surgical tool is packaged under sterile conditions in a plastic package; the package is made up of at least two parts and consists of an inner protective packaging for sensitive parts of the surgical tool and a sealable blister packaging that accommodates the protective packaging. Furthermore, a method for packaging sterile surgical tools is proposed in which the surgical tool is packaged in the plastic packaging under sterile conditions, wherein in a first step, the surgical tool is first packaged at least partially and in particular with its sensitive cutting edges and working surfaces in the first protective packaging, and the protective packaging is transferred together with the surgical tool packaged there into a second blister packaging, where it is secured in position and then sealed with a sealing film. However, the problem of contamination of the product when it is removed from the package, as described above, also exists in this case.

SUMMARY

Against this background, the present invention is based on the object of reducing the aforementioned disadvantages of the prior art, and in particular to provide a package for a medical product with which the risk of negative consequences, such as inflammation, allergic reactions and the like, for a patient due to entrained abrasion can be minimized.

This object is solved according to the present invention by a package, in particular a sterile package, for a medical product, having a receiving space for the medical product, wherein a portion of the package facing the receiving space consists at least partially, preferably completely, of a resorbable material. The preceding object is furthermore solved by a packaging unit comprising a package according to the invention, and a medical product arranged in the receiving space.

In the scope of the invention, the product may in particular be a product having a working end in the broadest sense. Such a working end may be, for example, a distal, generally sharp-edged operative portion for performing an operative function of a tool/surgical tool further comprising a proximal coupling portion for coupling the tool to a handle unit, in particular a drive handle unit. Examples of such tools are, in particular, rotating tools as well as sawing tools, including, but not limited to, drills, milling cutters, saws, screw adapters, cutting blades or grinding adapters, which are coupled to a handle and/or drive unit in a generally known manner. Further examples of a product in the sense of the invention are instruments with an atraumatic effect, such as HF syringes or ultrasonic blades. In addition, the product may be an implant of any type and shape, such as bone implants, joint implants or partial implants, stents, etc. Such implants often have a sharp-edged operative portion, for example in the form of a thread or the like.

According to the invention, the product is insertable or inserted into the package, which is at least partially made of a resorbable material. According to the invention, the entire package or only a part thereof may consist of the resorbable material. If only partial areas of the package consist of resorbable material, these partial areas are preferably arranged and formed in such a way that contact of the product with parts of the package not consisting of resorbable material can be reliably avoided during insertion, holding/storage and removal of the product. Thus, in a case where contact occurs between the product and the package, and material particles of the package adhering to the product are carried into the body of a patient unnoticed, a negative influence on the patient can be reliably prevented or at least reduced, since the material particles possibly adhering to the product are degraded in an advantageous manner by the body of the patient. Preferably, the package consists entirely of a resorbable material. A resorbable material within the meaning of the invention is to be understood in particular as a material which can be decomposed and degraded and possibly excreted by the human or animal body, in particular into components which are harmless to the body, such as water and carbon dioxide.

An embodiment of the invention is characterized in that the package comprises an outer packaging. Additionally, it may comprise a holding device arranged in the receiving space. Such a holding device may advantageously be arranged and/or held in a positionally determined manner in the receiving space. It serves in particular to hold the product, in particular to hold it in a positionally determined manner and to position it in the receiving space in such a way that contact of sharp operative portions with the package material is avoided and that sharp operative portions are spaced from the package. By providing such a holding device, contact of the product with parts of the package can be prevented or at least safely minimized, so that abrasion of package material by the product can be prevented. Preferably, the holding device and/or the outer packaging may consist at least partially, preferably entirely, of a resorbable material.

According to a further embodiment, the holding device and/or the outer packaging may be provided with a coating of the resorbable material in its region bounding the receiving space. This has the advantage that the package can be produced particularly simply and inexpensively with the respectively desired properties, such as weight, stability, size, etc., wherein, nevertheless, risks for the patient due to a transfer of packaging material into the patient's body can be safely avoided. The thickness of the coating is preferably such that, in the event of contact between the product and the outer packaging and/or holding device, there is no abrasion of non-resorbable material. A particular advantage is that in this embodiment of the invention, the outer packaging and/or the holding device can be designed largely independently of the mechanical properties of the resorbable material, so that existing and proven designs of such packages can be largely adopted within the scope of the invention. In an advantageous further development of this embodiment, the coating may thereby be applied to the holding device and/or the outer packaging in the form of a foil coating, i.e. a second, resorbable material that is different from the material of the holding device and/or the outer packaging may be applied to the holding device and/or the outer packaging, for example by welding or bonding. In other words, the holding device and/or the outer packaging can be coated with this second material or foil, so that the layer thickness of the resorbable material can be easily controlled and thus larger layer thicknesses can also be realized.

The resorbable material in the sense of the invention may be a resorbable biopolymer or a copolymer thereof, in particular a resorbable polyester, gelatin, thermoplastic starch (TPS) or compositions or mixtures thereof. Preferably, the resorbable material in the sense of the invention is a polylactide (PLA), in particular a polylactide of the chemical formula $(C_3H_4O_2)_n$-O—CO—CH(CH4), in particular a poly-L-lactide (PLLA), a poly-D-lactide (PDLA) or a poly-DL-lactide (PDLLA), PCL (polycaprolactone), PHB (polyhydroxybutyric acid) or a composition or mixture of the aforementioned materials. These resorbable materials not only ensure controllable and safe biodegradation in the body, but are also highly tissue compatible. In the case of PLA, water present in the patient's body breaks down the polymer chains of this material and the human metabolism ultimately converts the D-lactides and L-lactides into carbon dioxide and water, so that material particles accidentally inserted into the patient's body are degraded in a particularly advantageous manner without leaving residues. The invention is particularly suitable for medical instruments and tools that have sharp-edged and sensitive operative contours or working contours, for example sharp cutting edges, blades, drilling, sawing and milling contours, which can particularly easily cause abrasion and adhesion of packaging material.

According to a further embodiment of the invention, it is provided that the holding device is formed separately from the outer packaging. Alternatively or additionally, the holding device can be designed to keep the product at a distance away from the outer packaging at least in certain areas, preferably completely. If the product is a medical product, it can be held at a distance from the outer packaging, in particular in the region of an operative portion of the tool. If the product is an implant with sharp-edged operative portions or structures, such as a thread, such structures can simply be kept at a distance from the outer packaging. In this way, abrasion of packaging material by the product can be easily limited or even prevented.

According to a preferred embodiment, at least the operative portion of the tool or any existing sharp-edged structures of the implant is/are exposed in the holding device and has neither direct contact with the holding device nor with the outer packaging. In other words, the holding device is open at least in the region of the operative portion of the tool/sharp-edged structures of an implant. This has the advantage, among other things, that the operative portion/sharp-edged structure is visible to a user almost without restriction, which facilitates identification of the tool/implant. In addition, the operative portion is freely accessible to media such as disinfectants and sterilants. This results in the great advantage that the package according to the invention is suitable for both sterilized and non-sterilized products. The latter can be removed from the outer packaging and then sterilized together with the holding device in a particularly advantageous manner.

According to an embodiment of the invention, the holding device is formed separately from the outer packaging. Therefore, the product/tool/implant held in the holding device can be removed together with the holding device from the outer packaging and can in particular remain in the holding device after unpacking until it is finally used. Preferably, the package and the holding device are designed in such a way that removal can take place by handling the holding device and without direct contacting of the product/tool/implant, so that the probability of contamination of the product/tool/implant can be easily and safely minimized, or even avoided altogether. Moreover, the product/tool/implant can be placed together with the holding device on an instrument table without having to put it down loosely. During a surgery or treatment, the holder can be used in a particularly advantageous manner for intermediate storage of the product/tool/implant, resulting in better organization and clarity.

Since at least the operative portion, preferably the entire product/tool/implant, is kept at a distance from the package, it is possible in a particularly advantageous way to reliably ensure contact-free storage in the area of the operative portion with respect to any cutting edges or sharp edges present therein. In particular, contact of the operative portion with all surrounding packaging components, such as blister, Tyvek film, carrier, etc., is not possible. Any undesirable mutual influence of outer packaging and product/tool/implant, such as material removal or perforation of the outer packaging or blunting or contamination can be reliably prevented.

Overall, the invention thus provides, in addition to the package in the actual sense, an independent holder in the form of the separate holding device, which, in addition to safe and stable storage of products/tools/implants during transport in the respective outer packaging, also enables defined positioning and safe handling of the tool during reprocessing (e.g. sterilization) as well as during preparation of the product during treatment in the operating room. For this purpose, the holding device can be removed from the outer packaging together with the product/tool/implant held in it and can be placed in position.

One embodiment of the invention is characterized in that the receiving space is formed by the outer packaging in a closed manner, in particular hermetically sealed. It can also be designed to be sterile. The invention and the holding device which holds the product/tool/implant at a distance from the package can ensure the sterility and integrity of the package in a simple and reliable manner.

According to an embodiment of the invention, the holding device comprises a base plate. In particular, this can be designed in such a way that it forms a footprint for position-stable placement of the holding device with a product held therein, in particular in a state unpacked from the package, and/or an abutment structure for abutment against the package. In addition to the footprint, the holding device may have further abutment structures or portions that interact with and abut on the package so as to ensure clear and stable orientation positioning in the receptacle of the package.

According to a embodiment of the invention, the holding device can have at least two holding structures spaced apart from each other for orientation-determined positioning of the product. Preferably, each of these is arranged on the base plate and may extend therefrom into the receiving space. In addition to the function of holding the product, the holding structures can form attachments with which the holding device rests against the package, preferably in such a way that its orientation is secured or fixed in the receptacle of the package.

One embodiment is characterized in that one of the holding structures is disposed at the end side of the holding device, in particular on the base plate. Another one of the holding structures can be arranged substantially centrally on the holding device, in particular on the base plate. This enables the product to be held in the holding device in a particularly stable manner.

Preferably, one of the holding structures is designed to position the product in an orientation-determined manner relative to the holding device in a first direction. The other one of the holding structures can be designed to position the product in an orientation-determined manner relative to the holding device in a second direction and a third direction, wherein the first, second and third directions are orthogonal to each other. By means of such guiding, the product is held stably in the holding device on the one hand, and on the other hand it can be arranged in the holding device and removed from the holding device particularly easily by a user.

It is particularly advantageous if, according to a further embodiment of the package, at least one of the holding structures forms a form fit and/or a force fit with the product, in particular with a coupling structure of the tool.

At least one of the holding structures, in particular both holding structures, can have two holding arms opposite each other. A slit is formed between each of these to receive and hold the product. The holding arms can be arranged essentially perpendicular to the base plate of the holding device. In a particularly advantageous manner, they can be designed as clamping arms and in particular have resilient properties in a direction transverse to the slit. Removal and arrangement of the product in the holding structures is particularly easy if, according to one form of the invention, the slit widens in the direction from proximal of the base to distal of the base. This favors largely risk-free handling of both unused and used instruments, so that in particular injury-free disposal of products in the holding structure is improved and the risk of infection which exists in principle is reduced.

According to a further developed embodiment of the invention, the sides of the holding arms facing the slit may be provided with indentations. Such indentations can advantageously form locking pockets for the product inserted in the slit, so that the product is held securely in the holding structures and yet can be easily removed by a user.

A particularly user-friendly embodiment of the invention, which avoids injuries of a user by the tool held in the holding device, provides that the holding device comprises a protective lug which protrudes from the base plate into the receiving space and covers a distal end of the tool or a sharp-edged structure of the product without contact. In this way, a user is protected from injury from any sharp edges of the product when handling the holding device with the product held therein.

According to an embodiment of the invention, the package is formed as a blister. Such blisters are inexpensive and can be manufactured for almost any shape of the product and/or holding device. Preferably, the blister packaging may have a lower shell with a recess forming the receiving space for the product. Such a lower shell can simply be formed with a stability and shape sufficient for the orientation-stable positioning of the holding device and product. By means of a lid foil arranged on the lower shell in a known manner, the receiving space can be closed in the desired manner, in particular hermetically and/or in a sterile manner.

According to a further embodiment of the invention, the package may comprise a carrier element, for example in the form of a sieve basket. It can be arranged in the package together with the holding device and the tool held thereon, in particular with a plurality of holding devices with the respective tool held thereon. By means of such a carrier element, several holding devices with products held therein can be handled particularly easily and simultaneously, for example, they can be sterilized and/or placed on an instrumentation table.

According to a further embodiment of the invention, the holding device can be coded, for example by having a colored design. In this way, the invention can in an especially simple way provide a system with which not only different products can be coded in a way that can be easily distinguished by a user, but also such coding or marking of certain products can be retained even after the product has been unpacked from the package and assigned to the respective product. In particular, tools that have already been unpacked and are ready for use on an instrumentation table or in a sterilization facility can be identified particularly easily and reliably by the user. Different products and/or holding devices can preferably be identified by means of different colors of the holding devices, for example with regard to their indication or to specific product groups, etc. In this way, incorrect combinations of products can be avoided by the coloring of the holding device, which is designed in particular as a plastic injection-molded part, in and outside the package.

According to a further embodiment of the invention, the holding device may be formed as a molded plastic part. If, according to a further developed embodiment of the invention, it is formed as a multi-component injection molding, it can be provided, for example, with a particularly good anti-slip footprint. This enables a stable arrangement of the holding device on an instrument table and/or on a carrier element such as a sieve basket during a processing operation. In addition, this can greatly facilitate the handling of the holding device when removing the unused products as well as when inserting a used tool.

BRIEF DESCRIPTION OF THE DRAWING FIGURES

Further features and advantages of the present invention will be apparent from the following exemplary and non-limiting description of the invention by means of figures. These are merely schematic in nature and serve only for understanding the invention. They show.

DETAILED DESCRIPTION

Figure 1:
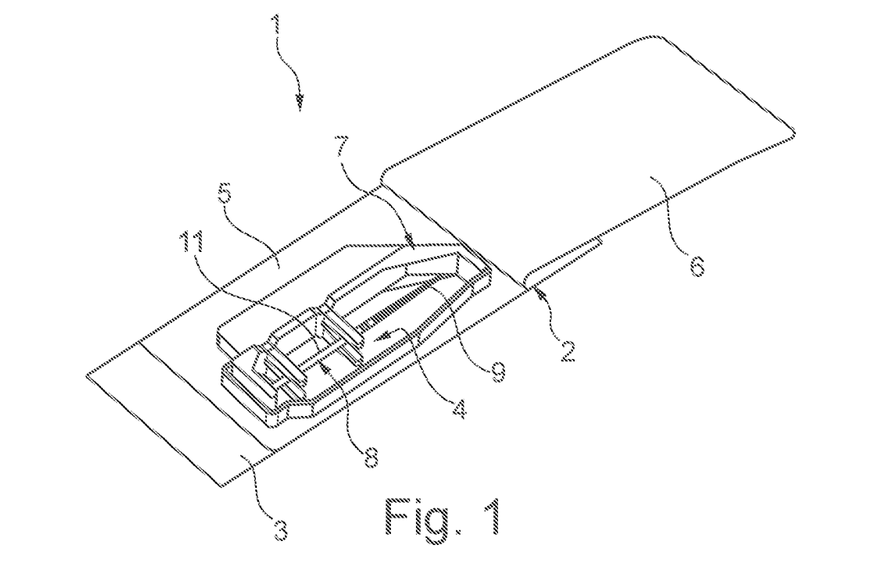
FIG. 1 shows a perspective view of an embodiment of a package according to the invention.
Figure 2:
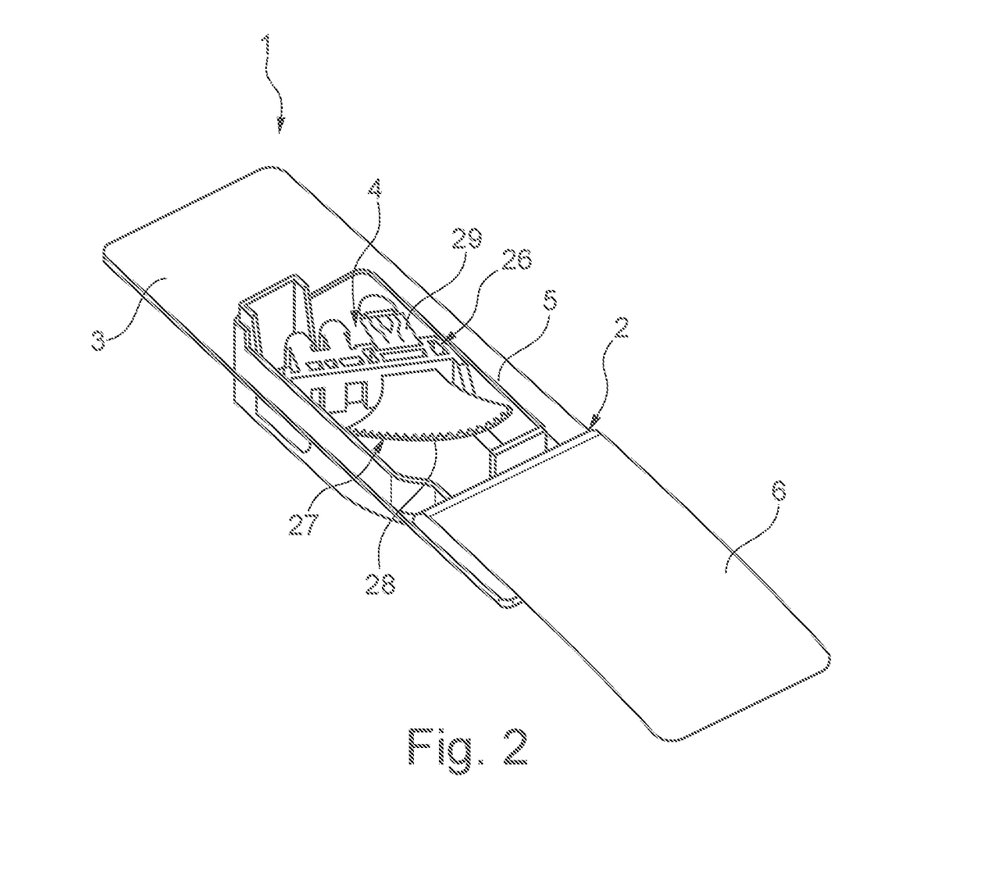
FIG. 2 shows a perspective view of an embodiment of a package according to the invention.

FIGS. 1 and 2 each show a embodiment of a package 1 according to the invention. This comprises an outer packaging 2 in the form of a blister 2 with a lower shell 3 with a recess 4 formed therein and an edge 5 surrounding the recess 4. The outer packaging 2 also comprises a lid foil 6 arranged on the surrounding edge 5 of the lower shell 3 and hermetically sealing the recess 4, said lid foil 6 being shown in FIGS. 1 and 3 respectively in a partially opened state. According to the invention, both the lower shell 3 and the lid foil 6 are made of a resorbable material.

Figure 3:
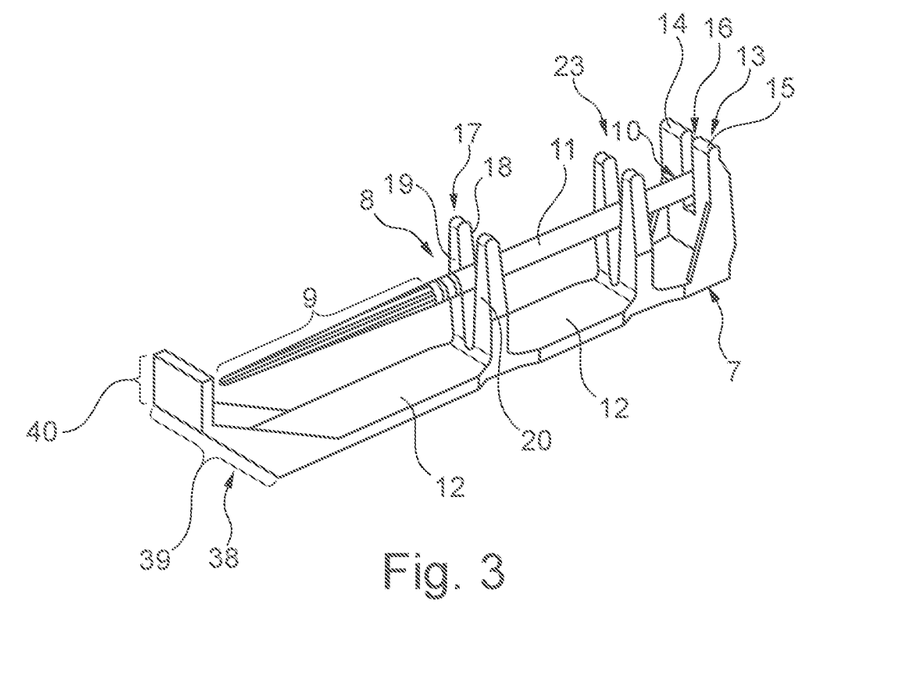
FIG. 3 shows a perspective view of a holding device with a tool held therein.

In the recess 4 of the outer packaging 2 of FIG. 1, a holding device 7 with a tool 8 held therein is arranged as an example of a packaged product (see also FIG. 3). The tool 8 in the present configuration example is a drill 8, at the distal end of which an operative portion 9 in the form of a drill head 9 is formed and at the proximal end of which a coupling structure 10 is formed for arranging the tool 8 in a tool accommodation (not shown) of a drive handle unit. The tool 8 has an elongated tool shaft 11 between the operative portion 9 and the coupling structure 10.

The holding device 7 of the embodiment of FIG. 1 is shown in FIG. 3 without the outer packaging 2. It is designed as a plastic molded part, consists entirely of a resorbable material and has a base plate 12. A first holding structure 13 is formed at the proximal end of the base plate 12. This holding structure 13 comprises two holding arms 14, 15, which are parallel to each other, extend from the base plate 12 essentially orthogonally in the direction of the tool 8 and which are connected to the base plate 12. A slit 16 is formed between the holding arms 14, 15 as a receptacle for the coupling structure 10 of the tool 8. A second holding structure 17 is formed centrally of the base plate 12, which extends from the base plate 12 in the same direction as the first holding structure 13. The second holding structure 17 also has two holding arms 19, 20 which are opposite each other and form a receiving slit 18 between them, and which are both arranged essentially orthogonally to the base plate 12. A third holding structure 23 is formed between the first holding structure 13 and the second holding structure 17, which is essentially similar to the second holding structure 17 and which is therefore not described further.

Figure 4:
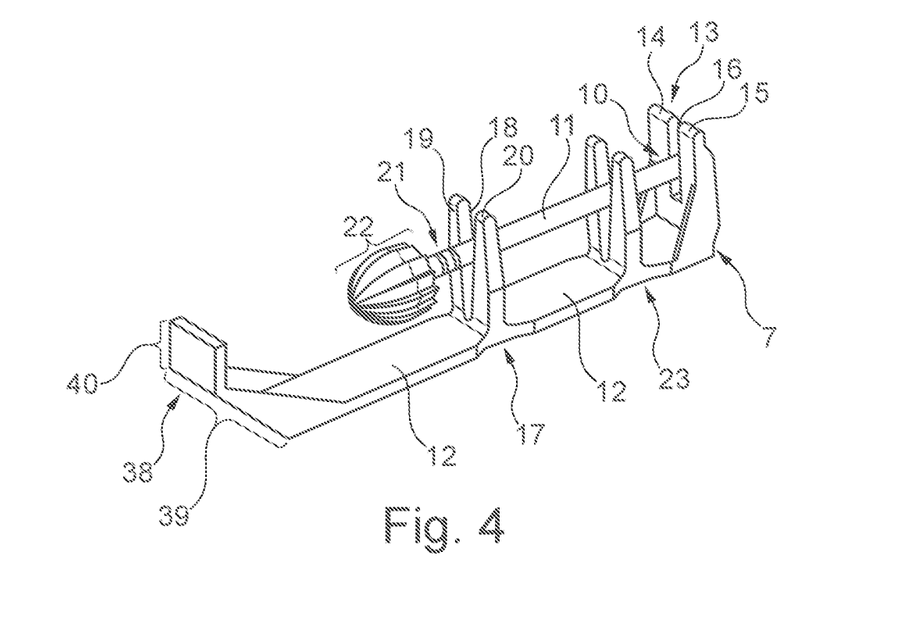
FIG. 4 shows a perspective view of a holding device with a tool held therein.

FIG. 4 shows the holding device 7 of FIG. 3 with another tool 21, here in the form of a milling adapter 21. Like the drill 8 of FIGS. 1 and 3, the milling adapter 21 has a coupling structure 10 and a tool shaft 11 and differs from the drill 8 in that its distal operative portion 22 is formed as a milling head 22. Nevertheless, the invention allows the drill 8 and the milling head 21 to be accommodated in the same holding devices 7.

Figure 5:
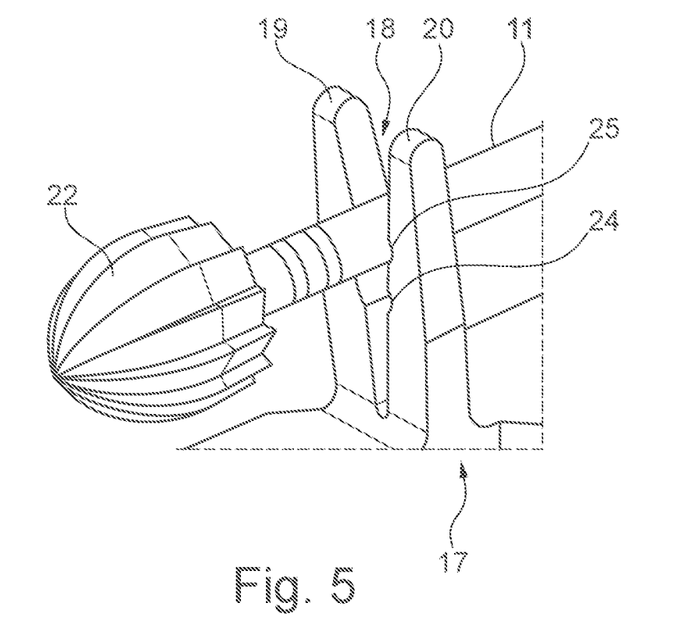
FIG. 5 shows an enlarged detail of FIG. 4.
Figure 7:
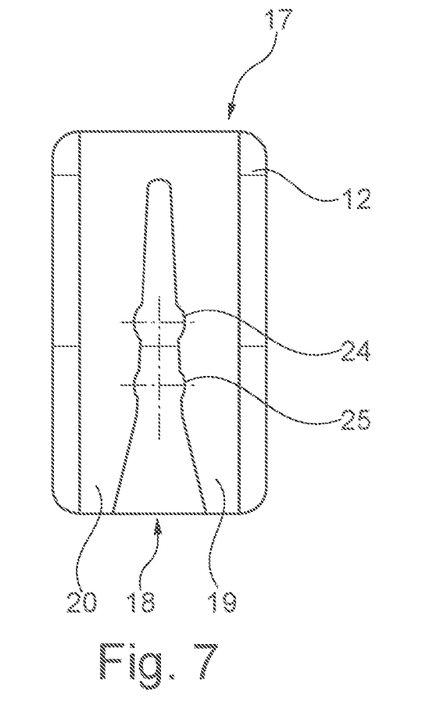
FIG. 7 shows a sectional view of a holding device through its holding structure transverse to the longitudinal axis.

FIG. 5 shows the second holding structure 17 of the holding device 7 in an enlarged detailed view. The side surfaces of the holding arms 19, 20 facing each other are each provided with two indentations 24, 25 of different sizes arranged one above the other, each for receiving tool shafts 11 of different diameters (see also FIG. 7, which shows the second holding structure 17 in a sectional view transverse to the longitudinal axis of the tool 8, 21). The holding arms 19, 20 have certain elastic spring properties and can perform a spring movement relative to each other, so that the slit 18 can widen when a tool 8, 21 is inserted and the holding arms 19, 20 spring back to their original position as soon as the shaft 11 of the corresponding tool 8, 21 is arranged in the indentation 24, 25. In this way, the tool 8, 21 is held securely in the holding device 7. In particular, it can be held clamped between the holding arms 19, 20.

Figure 8:
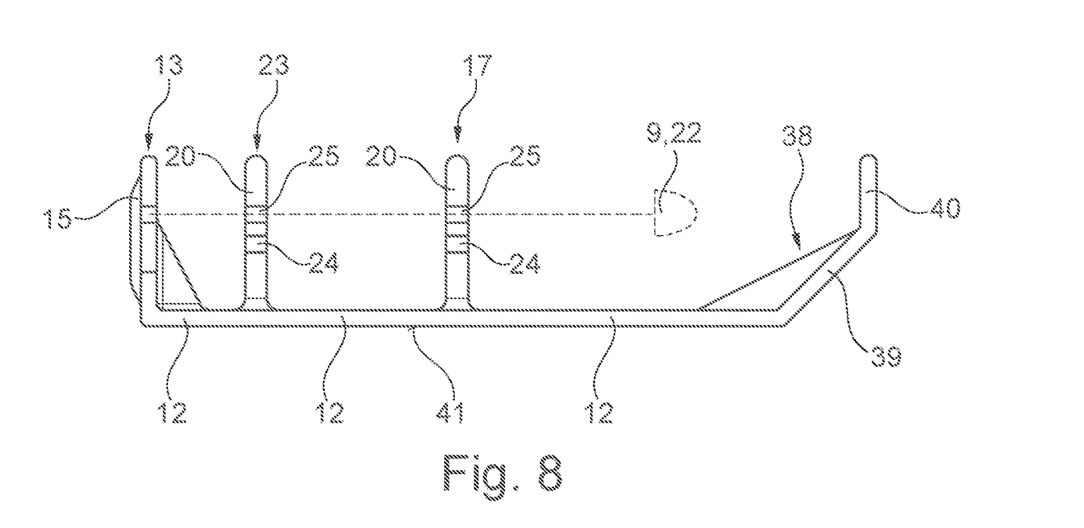
FIG. 8 shows a sectional view of a holding device in the direction of the longitudinal axis.

A protective lug 38 is arranged at the end (operative-portion side) of the base plate 12 opposite the first holding structure 13. The protective lug 38 projects from the base plate 12 first with an inclined portion 39 at an oblique angle (here of about 45°) and is then bent by a further angle to an end portion 40, so that its end facing away from the base plate 12 is arranged approximately transversely to the latter. As in particular FIG. 8 shows, the protective lug 38 projects from the base plate 12 to such an extent that the respective distal end of the operative portion 9, 22 is covered without contact. This design of the protective lug 38 creates a good grip possibility in the form of the inclined portion 39 for being grasped by a user, for example from the position shown in FIG. 6 from an instrumentation table, wherein the operative portion is covered so that its contacting by the user can be safely prevented and thus a risk of injury can be minimized. A further aspect of the inclined portion 39 may be that this inclination serves, according to the principle of poka-yoke, in the context of manufacturing/packaging to be able to place the holding device 7 in the right position and the right way around in the outer packaging 2.

Figure 6:
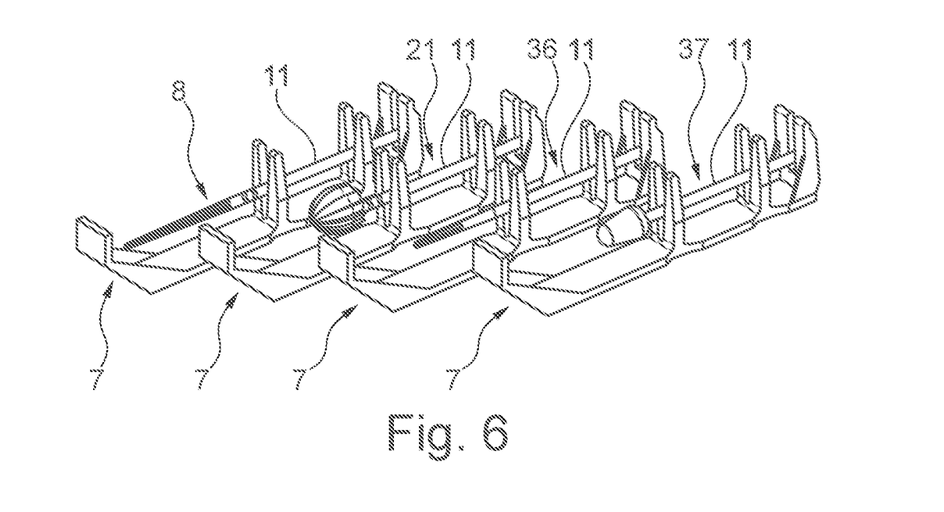
FIG. 6 shows a plurality of holding devices, each with a tool held therein.

FIG. 6 shows that the holding device 7 is suitable for receiving and holding different tools 8, 21 as long as they have a substantially similar basic shape with a shaft 11 and a coupling structure 10 at the proximal end and actually differ only with respect to their respective operative portion 9, 22. Exemplarily shown in FIG. 6 are the drill adapter 8, the milling adapter 21, a screwing adapter 36 and a sanding/grinding adapter 37, wherein the shaft diameters of the adapters 36, 37 are smaller than those of the adapters 8, 21, so that the adapters 36, 37 are arranged in the indentation 24 with smaller diameter and the adapters 8, 21 are arranged in the indentation 25 with larger diameter. Furthermore, it can be seen from FIG. 6 as well as from FIG. 3 that the holding device 7 (the same applies to the holding device 26 described below), in addition to fixing the position of the tool 8, 21 in the packaged state, i.e. in the state shown in FIGS. 1 and 2, can be used as a holding device which can be used separately from the outer packaging 2, in order to set down the tool, for example when it is provided in the course of an operation or during sterilization. The lower side 41 of the base plate 12, 30 forms a footprint 41 for this purpose, on which the holding device 7, 26 with a tool held therein can be placed in a stable manner.

A holding device 26 with a tool 27 held therein is arranged in the recess 4 of the outer packaging 2 of FIG. 2. The tool 27 is in the present configuration example a sawing adapter 27, at the distal end of which an operative portion 28 in the form of a saw blade and at the proximal end of which a coupling structure 29 are formed for arranging the tool 27 in a tool accommodation (not shown) of a drive handle unit.

Figure 9:
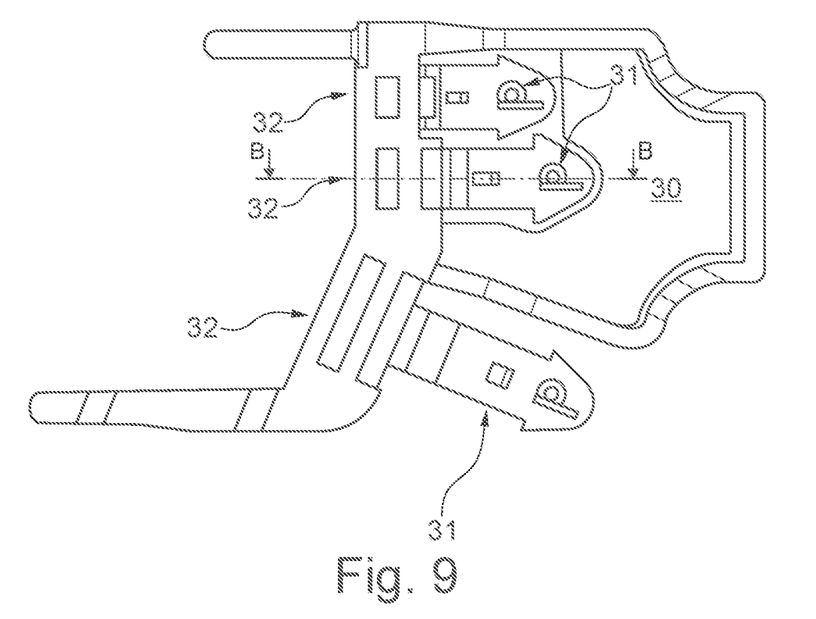
FIG. 9 shows a top view of the holding device of FIG. 2.
Figure 10:
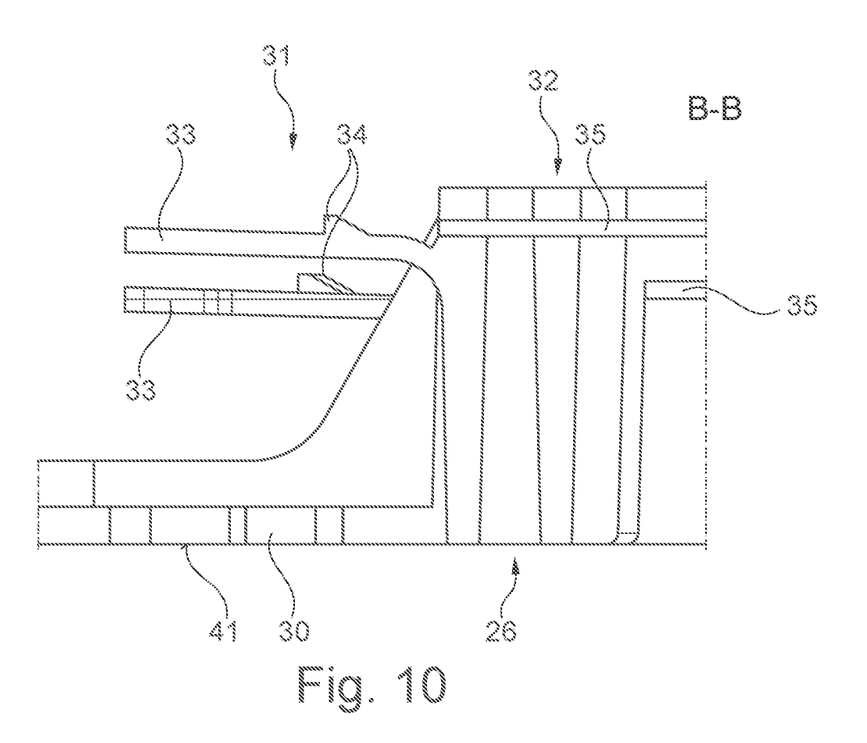
FIG. 10 shows a sectional view of the holding device of FIG. 9.

As shown in FIGS. 9 and 10, the holding device 26 comprises a base plate 30. Arranged on the base plate 30 are a first holding structure 31 and a second holding structure 32, which are spaced apart from the base plate 30 in a direction transverse to the latter. The holding device 26 of FIGS. 9 and 10 is provided with a total of three first and three second holding structures 31, 32 in order to be able to accommodate sawing adapters of different shapes and/or sizes. The three different holding structures 31, 32 are basically similar in design, so that only one of each will be described below. It should be noted that the number of three holding structures is only exemplary, and the holding device 26 may have a different number of holding structures within the scope of the invention.

The first holding structure 31 has a spring arm 33 which can perform a spring movement in the direction towards the base plate 30. On its side facing away from the base plate 30, the spring arm 33 is provided with a latching structure 34, here in the form of a snap-in nose 34, which can interact with the coupling structure 29 of the sawing adapter 27 and can thus fix the latter in position relative to the second holding structure 32 and in a direction parallel to the base plate 30. The second holding structure 32 is formed as a slit 35 through which the coupling structure of the sawing adapter 27 can be pushed until it engages with the first holding structure 31 and the snap-in nose 34. The slit 35 is dimensioned such that the sawing adapter 27 is positioned in an orientation transverse to the base plate 30 and in the remaining direction parallel thereto. The slit 35 and the spring arm 33 are designed and positioned relative to each other in such a way that the sawing adapter 27 can only be brought into its intended position, in which it is latched with the snap-in nose 34, by springing in the spring arm 33.

In order to remove the sawing adapter 27, the spring arm 33 is to be manually deformed by an operator in the direction of the base plate 30 in such a way that the coupling structure of the sawing adapter 27 can be released from the snap-in nose 34 and the sawing adapter 27 can be pulled out of the slit 35 in a direction parallel to the base plate 30. A used sawing adapter 27 can be particularly easily arranged again in the holding device 26 for intermediate storage and/or disposal by simply pushing it again in the direction of the snap-in nose 34 through the slit 35, wherein the spring arm 33 deflects until the snap-in nose 34 engages with the coupling structure 29 of the sawing adapter 27 and the latter is secured in position in the holding device 26.

The invention claimed is:

1. A package for a medical product, comprising a receiving space for the medical product,
wherein
a portion of the package facing the receiving space at least partially comprises resorbable material, and
the package has an outer packaging and a holding device arranged in the receiving space, in which the product is held.

2. The package according to claim 1, wherein the holding device and/or the outer packaging at least partially comprises resorbable material and/or is or are provided with a coating of the resorbable material, at least in their region adjacent to the receiving space.

3. The package according to claim 1, wherein the resorbable material is a biopolymer or a copolymer thereof, or the resorbable material is selected from the group consisting of: gelatin, thermoplastic starch, polyester, polylactide, polycaprolactone and polyhydroxybutyric acid.

4. The package according to claim 1, wherein the holding device is designed separately from the outer packaging and/or the holding device is designed to keep the product, at least in regions, spaced apart from the outer packaging.

5. The package according to claim 1, wherein the holding device has a base plate which forms a footprint for placing the holding device, with a product held therein in a positionally stable manner, and/or which forms a contact structure for contact with the outer packaging.

6. The package according to claim 5, wherein the holding device comprises at least two holding structures spaced apart from each other for position-determined positioning of the product.

7. The package according to claim 6, wherein at least one of the holding structures has two holding arms which are located opposite each other and between which a slot is formed for receiving and holding the product in a clamping manner.

8. The package according to claim 7, wherein the slot widens from a proximal direction of the base plate towards a distal direction of the base plate.

9. The package according to claim 1, wherein the holding device comprises a protective lug which projects from the base plate into the receiving space and covers a distal end of the product without contact.

10. The package according to claim 1, wherein the outer packaging is designed as a blister, comprising a lower shell which has a depression forming the receiving space, and comprising a lid film arranged thereon and closing the receiving space.

11. A packaging unit comprising a package according to claim 1 and a medical product arranged in the receiving space.

\* \* \* \* \*